US010030056B2

(12) United States Patent
Funke et al.

(10) Patent No.: US 10,030,056 B2
(45) Date of Patent: *Jul. 24, 2018

(54) AGENTS FOR PREVENTING AND TREATING HIV AND OTHER VIRAL INFECTIONS

(71) Applicant: FORSCHUNGSZENTRUM JUELICH GMBH

(72) Inventors: Susanne Aileen Funke, Sonnefeld (DE); Dieter Willbold, Juelich (DE); Heiner Schaal, Cologne (DE); Marek Widera, Duesseldorf (DE)

(73) Assignee: Forschungszentrum Juelich GmbH, Juelich (DE)

( * ) Notice: Subject to any disclaimer, the term of this patent is extended or adjusted under 35 U.S.C. 154(b) by 32 days.

This patent is subject to a terminal disclaimer.

(21) Appl. No.: 14/787,130

(22) PCT Filed: Apr. 17, 2014

(86) PCT No.: PCT/DE2014/000203
§ 371 (c)(1),
(2) Date: Oct. 26, 2015

(87) PCT Pub. No.: WO2014/177127
PCT Pub. Date: Nov. 6, 2014

(65) Prior Publication Data
US 2016/0122401 A1 May 5, 2016

(30) Foreign Application Priority Data

Apr. 30, 2013 (DE) .................. 10 2013 007 405
Sep. 26, 2013 (DE) .................. 10 2013 016 002
Mar. 12, 2014 (DE) .................. 10 2014 003 262

(51) Int. Cl.
| | | |
|---|---|---|
| *C07K 14/47* | (2006.01) | |
| *A61K 38/10* | (2006.01) | |
| *A61K 38/12* | (2006.01) | |
| *A61K 38/16* | (2006.01) | |
| *A61K 9/20* | (2006.01) | |
| *A61K 9/06* | (2006.01) | |
| *A61K 9/00* | (2006.01) | |
| *C07K 7/08* | (2006.01) | |
| *A61K 38/00* | (2006.01) | |

(52) U.S. Cl.
CPC ............ *C07K 14/47* (2013.01); *A61K 9/0019* (2013.01); *A61K 9/06* (2013.01); *A61K 9/20* (2013.01); *A61K 38/10* (2013.01); *A61K 38/12* (2013.01); *A61K 38/16* (2013.01); *C07K 7/08* (2013.01); *C07K 14/4711* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2004/0034888 A1* | 2/2004 | Liu ...................... | C07K 14/415 800/289 |
| 2007/0231331 A1 | 10/2007 | Dewji et al. | |
| 2010/0204085 A1* | 8/2010 | Eisenberg ................ | C07K 7/06 514/1.1 |
| 2013/0157924 A1* | 6/2013 | Dewhurst ............ | A61K 31/428 514/1.1 |

FOREIGN PATENT DOCUMENTS

| | | | |
|---|---|---|---|
| DE | 10 2005 049 537 | 4/2007 | |
| DE | 10 2012 102 998 | 10/2013 | |
| DE | 10 2012 102 999 | 10/2013 | |
| EP | 1 379 546 | 1/2004 | |
| EP | 2 179 722 | 10/2008 | |
| WO | WO 02/081505 | * 10/2002 | ............ A61K 38/00 |
| WO | WO-02/081505 | 10/2002 | |
| WO | WO-2005/060352 | 7/2005 | |
| WO | WO-2010/041252 | 4/2010 | |
| WO | WO-2011/133929 | 10/2011 | |

OTHER PUBLICATIONS

Yang et al., 2012, Vaginal Gel Formulation Based on Theaflavin Derivatives as a Microbicide to Prevent HIV Sexual Transmission, AIDS Research and Human Retroviruses, 28(11): 1498-1508.*
Yang et al., 2012 (epub Sep. 11, 2012), Vaginal Gel Formation Based on Theaflavin Derivatives as a Microbicide to Prevent HIV Sexual Transmission, AIDS Research and Human Retroviruses, 28(11): 1498-1508.*
Volkmann et al., 1998, Biosynthesis of D-amino acid-containing peptides: Exploring the role of peptide isomerases, D-amino acids in Sequences of Secreted Peptides of Multicellular Organisms, EXS, 85: 87-105.*
Fischer, 2003, The Design, Synthesis and Application of Stereochemical and Directional Peptide Isomers: A Critical Review, Current Protein and Peptide Science, 4: 339-356.*
German Office Action dated Feb. 3, 2014 for DE 10 2013 007 405.3.
Christina C. Capule, et al.; Oligovalent Amyloid-Binding Agents REduce SEV1-Mediated Enhancement of HIV-1 Infection; Journal of the American Chemical Society 2012, 134+ S. 905-908.
Stuart A. Sievers, et al: Structure-based design of non-natural amino-acid inhibitors of amyloid fibril formation Nature, Jul. 7, 2011, vol. 475, S. 96-99.
Woj M. Wojtowiczl, et al: Stimulation of Enveloped Virus Infection by B-Amyloid Fibrils The Journal of Biological Chemistry, Sep. 20, 2002, vol. 277, S. 35019-35024.
Semen-Derived Amyloid Fibrils Drasticall Enhance HIV Infection Cell 131, 1059-1071, Dec. 14, 2007; Jan Muench et al.

(Continued)

*Primary Examiner* — Amber D Steele
(74) *Attorney, Agent, or Firm* — Norris McLaughlin & Marcus, P.A.

(57) ABSTRACT

An agent for preventing and/or treating HIV and other viral infections. The agent in particular comprises at least one peptide, including an amino acid sequence, which is suitable for preventing fibrils associated with Alzheimer's disease, and/or homologs, fractions and parts thereof, so as to treat and/or prevent HIV and/or other viral infections.

13 Claims, 7 Drawing Sheets

(56) References Cited

OTHER PUBLICATIONS

Comparison of Biosequences Temple F. Smith and Michael S. Waterman Advances in Applied Mathematics 1, pp. 482-489 (1981).

* cited by examiner

FIG. 1D (continuation)

FIG. 1E (continuation)

FIG. 2D (continuation)

AGENTS FOR PREVENTING AND TREATING HIV AND OTHER VIRAL INFECTIONS

The invention relates to agents for preventing and treating HIV and other viral infections.

BACKGROUND OF THE INVENTION

The human immunodeficiency virus, HIV for short, belongs to the retrovirus family and to the lentivirus genus. An HIV infection when left untreated generally results in acquired immunodeficiency syndrome (AIDS) following a variably long incubation period, which typically takes several years. Over the past 30 years, the spread of HIV has evolved into a pandemic, which according to estimates of the UNAIDS organization has cost some 28 million lives so far. At the end of 2010, an estimated 34 million people worldwide were infected with HIV. With the exception of one isolated case that has been described, the disease is not curable as of yet and requires lifelong treatment, which suppresses the infection-related symptoms by inhibiting HIV replication.

According to the German-Austrian guidelines for antiretroviral therapy of HIV infection, the goal of antiretroviral therapies (ART) is to suppress infection-related symptoms and mitigate the progression of the disease by inhibiting HIV replication. The prognosis of patients infected with HIV can be considerably improved using highly active antiretroviral therapy (HAART). Patients today are achieving a relatively high age. The therapy, however, must be conducted for life since the viral infection is generally only suppressed, but not cured. The physical and mental stress resulting from the permanent need to take drugs and from an increased frequency of infections is high, as are the costs of years of HAART. While HAART lowers the risk of infection for HIV due to a reduced viral load, an infection cannot be avoided. It is therefore desirable to prevent infection.

The HI virus is transmitted via contact with body fluids such as blood, semen, vaginal secretion, and breast milk. The most common routes of infection are sex without the use of condoms and unsterile syringes during intravenous drug use. Despite the high significance of semen in the sexual transmission of HIV, little is known about the routes of transmission.

In 2007, amyloidogenic proteins contained in seminal fluid, referred to as semen-derived enhancer of virus infection (SEVI), were reported, which were able to amplify the HIV infection of various cell types in cell culture and tissue models. These potentially play an important role in the sexual transmission of HIV since they may facilitate the contact between the virus and the host cell (Münch et al., Cell 131, 1059-1071).

Conversely, it should be possible to prevent the sexual transmission of HIV by preventing SEVI-HIV cell interaction. Initial experimental approaches on the prevention of SEVI-mediated HIV infection through the use of amyloid-binding substances in cell culture were already presented (Capule et al., JACS 134, 905-908). Development has not yet progressed greatly.

D-peptides are known from the published prior art Sievers et al. (Nature (2011). 475, 96-100) which bind to a hexapeptide (residues 306-311) of the tau protein, which is associated with Alzheimer's disease. In addition, an L-peptide is known from this published prior art, which likewise binds to a hexapeptide of the $^{248}PAP^{286}$ protein of human sperm. The respective fibril formation was able to be prevented specifically by way of the D-peptide for the tau protein, and by way of the L-peptide for the PAP protein.

Wojtowicz et al. In the year 2002 reported that synthetic, amyloid fibrils made up of $A\beta_{1-40}$ and $A\beta_{1-42}$ are able to enhance the infectivity of the HIV-1 virus (The Journal of Biological Chemistry (2002). 277, 35019-35024). $A\beta$ fibrils result in a 5- to 20-fold increase in infection efficiency of reporter cells expressing the HIV-1 receptor CD4.

SUMMARY OF THE INVENTION

It is the object of the invention to provide agents for preventing and treating HIV and other viral infections. Possible target molecules for preventing an infection are in particular, but not exclusively, SEVI fibrils in semen. In individuals already infected, the objective is in particular, but not exclusively, to prevent the development of HIV-associated neurological damage to the central nervous system (such as "HIV-associated dementia," HAD), or to slow progression of the same, by reducing the number of amyloid fibrils (composed of $A\beta$, for example), which steadily increases in the CNS with rising age, and thereby reduce the infection efficiency of HIV to an extent as great as possible.

The object of the invention is achieved by agents according to the main claim, use of the same, and by the microbicidal gel, the tablet and the respective uses of the same according to the additional independent claims.

The object is achieved by an agent that is suitable for preventing the formation of amyloid fibrils or for destroying the same.

According to the invention, the agent comprises at least one substance that is suitable for inhibiting the formation of amyloid fibrils, which increase the infection efficiency of a virus, or for destroying the same, so as to treat and/or prevent the particular viral infection.

For example, suitable agents are substances, among other things peptides, that contain at least one amino acid sequence developed or invented for the prevention and treatment of Alzheimer's disease in that peptides, comprising this sequence, prevent the formation of amyloid fibrils associated therewith or destroy the same. These may also be homologous sequences, fragments, and parts thereof. Non-peptidic agents, which are suitable for preventing the formation of amyloid fibrils or for destroying the same, are also suited. According to the invention, these are then used to treat and/or prevent HIV and/or other viral infections. According to the invention, they are used in particular to prevent the infection from spreading further in the body, such as in the CNS, or to treat the same.

Agents according to the invention preferably fully reduce the infectivity of viruses, which is increased by amyloid fibrils (such as $A\beta_{1-42}$ or SEVI fibrils). They lower the infectivity of viruses, such as HIV, increased by fibrils in particular by 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, wherein any intermediate value is possible. Agents according to the invention, in particular the peptides according to SEQ ID NO: 1 to 11, lower the increased infectivity by at least 50%, preferably by at least 60%, particularly preferably by at least 70%, and most particularly preferably by at least 80% or 90%, or at least 95%.

It was found that existing HIV infections generally have severe side effects. Active ingredients against the reverse transciptase have the drawback of also impairing other vital molecules, such as the DNA polymerase. As a result, cells undergoing frequent division, such as hair follicle cells and hematopoietic cells, are particularly affected (anemia). Agents according to the invention, and more particularly the peptides according to SEQ ID NO. 1 to 11, have no side effects on the DNA polymerase or on the cells of the hematopoietic system.

By comparison, the agents according to the invention advantageously achieve that the active ingredients contained therein, and more particularly the peptides according to SEQ ID NO. 1 to 11, are free from side effects. These advantageously cause only the formation of amyloid fibrils having an infection-enhancing effect to be prevented, or for the same to be destroyed, without affecting the monomers of which these are composed and which potentially have a positive function in the body.

An agent according to the invention, comprising at least one substance that is suitable for inhibiting the formation of Aβ fibrils in particular, or for destroying the same, is used to treat and/or prevent HIV and/or other viral infections and secondary diseases, such as HAD, by preventing the formation of amyloid fibrils, which increase viral infection efficiency, or destroying the same.

An agent according to the invention, comprising at least one peptide that includes an amino acid sequence and is suitable for preventing and treating fibrils associated with Alzheimer's disease, and/or homologs, fractions and parts thereof, is used to treat and/or prevent HIV and/or other viral infections and secondary diseases, such as HAD, by preventing the formation of amyloid fibrils, which increase viral infection efficiency, or by destroying the same.

In one embodiment of the invention, the peptide according to the invention is a peptide comprising at least one amino acid sequence that binds to amyloid-beta species, such as to $Aβ_{1-42}$, and the free C-terminus of which, which is to say the C-terminal carboxyl group, is modified so that the C-terminus does not carry a negative charge, but instead is neutral or has one or more positive charges.

The peptides according to the invention also include those peptides comprising at least one peptide binding to an amylold-beta species, wherein the peptide includes a linear amino acid sequence which enables it to bind to A-beta, such as to $Aβ_{1-42}$, and this property is either preserved or amplified by the peptide being present in cyclized form by a covalent bond at the two ends thereof.

Such peptides according to the invention particularly advantageously also achieve the object by providing a peptide having no excess negative charge at the C-terminus. This advantageously causes the peptide to be able to bind with higher affinity to the constituents of amyloid fibrils, such as SEVI or Aβ, and destroy these, as compared to a peptide comprising a carboxyl group at the free C-terminus.

In one embodiment of the invention, such peptides according to the invention are modified in the physiological state, in particular at pH 6 to 8, in particular 6.5 to 7.5, in particular at pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9 or pH 8.0, or the intermediate values thereof, so that the C-terminus does not carry a negative charge, but instead is neutral or has one or more positive charges.

In a further embodiment of the invention, the peptide is characterized in that an acid amide group is present at the free C-terminus in place of the carboxyl group. Instead of the carboxyl group (—COOH group), an acid amide group (—CONH$_2$ group) is thus provided at the C-terminus. The peptide is thus particularly advantageously amidated at the free C-terminus. This particularly advantageously achieves the further object that a peptide having no excess negative charge is present, which can bind with higher affinity to the target molecule, which is to say to A-beta fibrils and/or fibrils associated with SEVI, and destroy these, and can be obtained in a simple manner.

In a further embodiment of the invention, the following further groups are present in place of the carboxyl group: COH, COCl, COBr, CONH-alkyl group, CONH-alkylamine group (positive net charge), and so forth, wherein there is no imitation to these, provided the technical teaching is followed, according to which the C-terminus does not carry a negative charge, but instead is neutral or has one or more positive charges.

The object of the invention is achieved in particular by peptides containing an amino acid sequence according to SEQ ID NO: 1 (D3), SEQ ID NO: 2 (RD2), SEQ ID NO: 3 (DB3), SEQ ID NO: 4 (D3r), SEQ ID NO: 5 (D3p), SEQ ID NO: 6 (D3) and/or homologs, fragments, and parts thereof. These peptides are substance units (hereafter often referred to as "monomers") that bind to amyloid-beta species.

In one variant of the invention, monomers are used which bind to the constituents of amyloid fibrils, such as SEVI or Aβ, with a dissociation constant ($K_D$ value) of no more than 500 µM, preferably 250, 100, 50 µM, particularly preferably 25, 10, 6 µM, and in particular 4, 2, 1 µM.

The object is also achieved in particular by polymers composed of two or more of the above-mentioned monomers, in particular dimers of SEQ ID NO: 7 (RD2D3), SEQ ID NO: 8 (D3RD2), SEQ ID NO: 9 (D3D3), SEQ ID NO: 10 (RD2RD2) and/or SEQ ID NO: 11 (DB3DB3) and/or homologs, fragments, and parts thereof. The dimers are composed of two monomer units, which bind to amyloid-beta species and/or fibrils associated with SEVI.

The polymers according to the invention, composed of monomers, which, in turn, bind to amyloid fibrils, such as of Alzheimer's disease or SEVI, or prevent the formation thereof or even destroy the same, exhibit clear, synergistic effects with respect to the selectivity and affinity thereof, compared to the monomers. In other words, the polymers according to the invention, in particular the dimers, selected from the group consisting of SEQ ID NO:7, SEQ ID NO: 8, SEQ ID NO: 9, SEQ ID NO: 10 and/or SEQ ID NO: 11, are superior to the monomers of which they are composed. Synergistic effects within the meaning of the present invention are effects that exhibit a higher selectivity and/or affinity with respect to the constituents of amyloid fibrils, such as SEVI or Aβ, in particular the $K_D$ value regarding the constituents of amyloid fibrils, such as SEVI or Aβ, compared to the individual monomer units.

In a further particularly advantageous embodiment of the invention, the polymers, and more particularly the dimers, (in vivo) advantageously act more efficiently than the monomers in the animal model experiment.

In one variant of the invention, polymers are used which bind to amyloid fibrils, such as of the A-beta peptide, with a dissociation constant ($K_D$ value) of no more than 500 µM, preferably 250, 100, 50 µM, particularly preferably 25, 10, 1 µM, particularly preferably with a dissociation constant ($K_D$ value) of no more than 500 nM, 250, 100, 50, particularly preferably 25, 10, 1 nM, 500 pM, 100, 50, 25, 10, 9, 8, 7, 8, 5, 4, 3, 2, 1 pM to sub-pM.

In one embodiment of the invention, the affinity is defined by way of the dissociation constant ($K_D$ value).

Fragments and parts exhibit a similar or identical effect as the peptides according to the invention.

In one variant, the peptides according to the invention, and more particularly the peptides according to SEQ ID NO: 1, SEQ ID NO: 2, SEQ ID NO: 3, SEQ ID NO: 4, SEQ ID NO: 5, SEQ ID NO: 6, SEQ ID NO: 7 and/or SEQ ID NO: 8, SEQ ID NO: 9, SEQ ID NO: 10 and/or SEQ ID NO: 11, and the homologs, fragments or parts thereof, are substantially, preferably at least 50%, 60%, 75%, 80%, particularly preferably 85%, 90%, 95%, in particular 96%, 97%, 96%, 99%, 100% composed of D-amino acids.

A polymer within the meaning of the invention is formed of 2, 3, 4, 5, 6, 7, 8, 9, 10, 11, 12, 13, 14, 15, 16, 17, 18, 19, 20 or more monomers that bind to constituents of amyloid fibrils, such as SEVI or Aβ.

The polymer is in particular composed of monomers selected from the group consisting of SEQ ID NO: 1, SEQ ID NO: 2 and/or SEQ ID NO: 3.

In one embodiment of the invention, the polymer may be selected from the group consisting of SEQ ID NO: 7, SEQ ID NO: 8, SEQ ID NO: 9, SEQ ID NO: 10 and/or SEQ ID NO: 11, and the homologs, fragments or parts thereof, which on their own already bind to amyloid beta oligomers of Alzheimer's disease.

In a further embodiment of the invention, peptides according to the invention comprise at least one peptide binding to an amyloid beta species, such as the D3 known from the related art, wherein the peptide comprises a linear amino acid sequence which enables the peptide to bind to A-beta, and this property is either preserved or amplified by the linear peptide being present in cyclized form by a covalent bond at the two ends thereof.

The described peptide D3 is known from WO 02/081505 A2, for example.

The peptide according to the invention advantageously comprises an amino acid sequence in which the cyclization of the linear molecule, which is to say the first one with the last amino acid, is carried out by a covalent bond, such as by way of a condensation reaction.

This measure advantageously results in no open ends of the peptide chain (amino acid sequence) being present.

A further result of this measure is that all linear peptides comprising amino acid sequences that, after cyclization, yield the same, no longer distinguishable amino acid order, are identical.

Example: The linear amino acid sequence of D3 is rprtrlhthrnr (SEQ ID NO: 1). The corresponding circularized peptide "cD3" linked between the N-terminal amino group and the C-terminal carboxyl group is no longer distinguishable from the circularized peptides having amino acid sequences with amino acid positions shifted 1, 2, 3, 4, 5, 6, 7, 8, 9, 10, or 11 positions to the right or to the left from D3.

The production of cyclized peptides is state of the art and can be carried out, for example, according to the methods as described in DE 102005049537 A1 or "Synthese von zyklischen Hexapeptiden mit Blutdrucksenkender Wirkung (Synthesis Of Cyclic Hexapeptides With Antihypertensive Effects" published by Beuth University of Applied Sciences Berlin.

The cyclization advantageously also means that there are no longer any "open" ends of the peptide chain, which often represent points of attack for peptide-decomposing activities in cells, animals or humans, such as by way of aminopeptidases and carboxypeptidases. Cyclized peptides thus advantageously have far greater stability in animals and humans than the corresponding linear peptides.

The cyclized peptide may comprise a linker group. The term linker group shall preferably be understood to mean additional individual amino acids in molecules, such as D3, which may be used per se in the treatment of Alzheimer's disease so as to bind A-beta constituents. The additional amino acid should not impair binding of the cyclized peptide to A-beta.

Several sequences, mentioned merely by way of example, of peptides that may be used according to the invention are listed below:

```
                                          (SEQ ID NO: 1)
    D3      rprtrlhthrnr (SEQ ID NO: 2)
    RD2     ptlhthnrrrrr (SEQ ID NO: 3)
    DB3     rpitrlrthqnr (SEQ ID NO: 4)
    D3r     rprtrlhthrnrr (SEQ ID NO: 5)
    D3p     rprtrlhthrnrp (SEQ ID NO: 6)
    D3a     rprtrlhthrnra (SEQ ID NO: 7)
    RD2D3   ptlhthnrrrrrrprtrlhthrnr (SEQ ID NO: 8)
    D3RD2   rprtrlhthrnrptlhthnrrrrr (SEQ ID NO: 9)
    D3D3    rprtrlhthrnrrprtrlhthrnr (SEQ ID NO: 10)
    RD2RD2  ptlhthnrrrrrptlhthnrrrrr (SEQ ID NO: 11)
    DB3DB3  rpitrlrthqnrrpitrlrthqnr
```

The monomeric peptide building blocks may be identical or non-identical.

The peptide building blocks may be linearly coupled head to head, tail to tail, or head to tail, and may overall be present in cyclized form by a covalent bond, with or without additional linker building blocks (such as one or more amino acids), of the two remaining ends, or amidated, or comprising other groups at the C-terminus.

The at least two peptide monomer units, in turn, may be covalently or non-covalently bonded to each other, for example by way of a biotin group or a streptavidin tetramer. The peptides are characterized by units that are linearly coupled head to head, tail to tail, or head to tail.

Since the target molecule of the therapeutic treatment is, for example, amyloid fibrils of Alzheimer's disease and/or fibrils associated with SEVI, or an amyloid beta oligomer, and thus naturally is a multivalent target, a particularly preferred embodiment of the invention uses substances that for a treatment, which is to say destruction of amyloid beta oligomers that are present, and more particularly amyloid fibrils of Alzheimer's disease and/or fibrils associated with SEVI, composed of multiple copies of an already efficient amyloid beta oligomer-binding unit, or of multiple different already efficient amyloid beta oligomer-binding units.

These peptides may be present in cyclized form. In this case, the peptide according to the invention comprises multiple peptide building blocks that, per se, effectively bind to amyloid beta oligomer, each being composed of amino acids, which are cyclized overall by a covalent bond.

In particular, all linear peptides comprising amino acid sequences that, after cyclization, yield the same, no longer distinguishable amino acid order, are identical. Example: The linear amino acid sequence of D3 is rprtrlhthrnr (SEQ ID NO: 1). The corresponding circularized peptide "cD3" linked between the N-terminal amino group and the C-terminal carboxyl group by an amide bond is no longer distinguishable from the circularized peptides having amino acid sequences with amino acid positions 1, 2, 3, 4, 5, 6, 7, 8, 9, 10, or 11 positions to the right or to the left from D3.

One variant of the invention relates to an agent comprising a peptide including the amino acid sequence according to SEQ ID NO: 1 and/or der SEQ ID NO: 2, SEQ ID NO: 3, SEQ ID NO: 4. SEQ ID NO: 5, SEQ ID NO: 6, SEQ ID NO: 7, SEQ ID NO: 8, SEQ ID NO: 9, SEQ ID NO: 10, SEQ ID NO: 11 and/or homologs thereof having an identity of 50%. Within the meaning of the invention, "homologous sequences" or "homologs" shall mean that an amino acid sequence has an identity of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% with one of the above-mentioned amino acid sequences of the monomers. Instead of the term "identity," the terms "homologous" or "homology" are used as synonyms in the present description. The identity between two nucleic acid sequences or polypeptide sequences is calculated by comparison with the aid of the BESTFIT program, based on the algorithm by Smith, T. F. and Waterman, M. S (Adv. Appl. Math. 2: 482-489 (1981)), setting the following parameters for amino acids: Gap creation penalty: 8 and Gap extension penalty: 2; and setting the following parameters for nucleic acids: Gap creation penalty: 50 and Gap extension penalty: 3. The identity between two nucleic acid sequences or polypeptide sequences is preferably defined by the identity of the nucleic acid sequence/polypeptide sequence over the entire respective sequence length, as it is calculated by comparison with the aid of the GAP program, based on the algorithm by Needleman, S. B. and Wunsch, C D. (J. Mol. Biol. 48: 443-453), setting the following parameters for amino acids: Gap creation penalty: 8 and Gap extension penalty: 2; and setting the following parameters for nucleic acids: Gap creation penalty: 50 and Gap extension penalty: 3.

Two amino acid sequences are identical within the meaning of the present invention if they have the same amino acid sequence. In one variant, homologs shall be understood to mean the corresponding retro-inverse sequences of the above-mentioned monomers. According to the invention, the term "retro-inverse sequence" denotes an amino acid sequence that is composed of amino acids in the enantiomeric form (inverse: chirality of the alpha carbon atom is inverted), and in which additionally the sequence order was reversed compared to the original amino add sequence (retro=reverse).

In a further variant, the peptides according to the invention also bind to parts of the amyloid beta peptide.

In a further variant, the agents according to the invention comprise peptides and sequences that differ from the indicated sequences by up to three amino acids.

Moreover, peptides having sequences that contain the above-mentioned sequences are used.

In a further variant, the peptides comprise fragments of the above-mentioned sequences or comprise homologous sequences with respect to the above-mentioned sequences.

Fragments and parts exhibit a similar or identical effect as the peptides according to the invention.

The agents according to the invention are used to treat and/or prevent HIV and/or other viral infections.

Polymers of peptides according to the invention comprising the described amino acid sequences, which are suitable for treating and/or preventing fibrils associated with Alzheimer's disease and the homologs thereof, also achieve the object of the invention. According to the invention, these are used to treat and/or prevent HIV and/or other viral diseases. According to the invention, these re agents comprising at least one substance that is suitable for inhibiting the formation of amyloid fibrils, such as Aβ fibrils, of Alzheimer's disease, or for destroying the same. These are used to treat and/or prevent HIV and/or other viral infections and secondary diseases, such as HAD, by preventing the formation of amyloid fibrils, which increase viral infection efficiency, or destroying the same.

According to the invention, the agents are used as therapeutic agents and to prevent HIV and other viral diseases.

The agent according to the invention, in a cream or a tablet dosage form, thus comprises a peptide, containing at least one amino acid sequence selected from the group consisting of SEQ ID NO. 1 and/or one of the listed SEQ ID NO: 2 to 11, or homologs or fragments and parts thereof, and polymers and the homologs, fragments and parts thereof. Other types of application, such as subcutaneous, intraperitoneal, intracranial, in the form of suppositories, as a nasal spray, and so forth, are likewise covered according to the invention. These forms of administration then include the agents according to the invention.

Further peptide sequences that can demonstrably be used to treat and prevent Alzheimer's disease can also be used to prevent HIV and other viral infections, or spreading of the same in the body, and are thus subject matter of the preset invention, since the targets of these are not only the amyloid fibrils of Alzheimer's disease, but optionally also the fibrils associated with SEVI.

It was found, within the scope of the invention, that possible target molecules for preventing an infection are, for example, but not exclusively, SEVI fibrils in semen. In people already infected, according to the invention, in particular but not exclusively, the development HAD may be prevented, or progression of the same may be slowed, by reducing the number of amyloid fibrils (composed of Aβ for example), which steadily increases in the CNS with rising age, and thereby decrease the infection efficiency of HIV to an extent as great as possible.

Within the scope of the invention, it was furthermore found that the peptides according to the invention, serving as constituents of the agents according to the invention, reduce the increase in efficiency of an HIV infection caused by amyloid fibrils, composed of SEVI or Aβ for example, and thus prevent an infection by way of sexual transmission and/or slow the spreading of the virus in the body. "Aβ" shall be understood to mean all species of human Aβ and the known variants and mutants described in people, such as $A\beta_{1-40}$, $A\beta_{1-42}$, $A\beta_{3-40}$, $A\beta_{pE3-40}$, $A\beta_{pE3-42}$, and mixtures thereof. Agents according to the invention prevent the formation of, or destroy, at least one of the described infection-enhancing amyloid fibrils.

Within the scope of the invention, it was found that only Aβ fibrils, and not Aβ monomers or Aβ oligomers, are able to increase HIV-1 infection. The invention thus, in particular, relates to those peptides according to the invention, serving as constituents of the agents, creams, tablets, suppositories, sprays and so forth, which are demonstrably used to treat and to prevent Alzheimer's disease by binding to and/or destroying the Aβ fibril, for example. These peptides, serving as constituents of the agents, creams, tablets, injection solutions and infusion solutions according to the invention, and so forth, can in particular also be used to prevent HIV and other viral infections, and are thus subject matter of the present invention.

It was furthermore found that peptides, such as the peptide D3 and the peptide D3D3 according to SEQ ID NO: 1 and SEQ ID NO: 9, respectively, particularly effectively eliminate the fibrils of Alzheimer's disease composed, among other things, of $A\beta_{1-42}$, as well as fibrils associated with amyloid sperm, as carriers and enhancers for viruses (SEVI), in particular retroviruses, such as HIV. It was surprisingly found that, despite the differing composition of the body's own fibrils, these apparently form similar structures so that these can be eliminated particularly effectively by way of a shared active ingredient, such as D3 according to SEQ ID NO. 1 or D3D3 according to SEQ ID NO. 9, or the remaining described agents.

The invention is not limited to these. The agents and peptide according to the invention are also able to effectively prevent other viral infections and the secondary diseases thereof, such as HAD.

The invention and the use of the agents according to the invention therefore relate not only to retroviruses, but also to rhabdoviruses, such as the human pathogenic vesicular stomatitis virus.

The use of the peptides according to the invention as a therapeutic agent and to prevent HIV, for example, and other, above-described viruses, is thus a direct subject matter of the invention.

A direct subject matter of the invention is in particular the use of the peptides according to the invention as a therapeutic agent or preventative agent for preventing the formation of, or for destroying, amyloid fibrils of Alzheimer's disease (Aβ fibrils) and SEVI fibrils which are present, so as to inhibit the HIV infection efficiency-increasing effect of the same.

There exist cross-effects of amyloid fibrils. Amyloid fibrils of Alzheimer's disease and/or of fibrils associated with SEVI, yet also fibrils composed of other proteins/peptides, can simultaneously be treated with agents according to the invention. Agents used against the amyloid fibrils of one disease can also be used against another, optionally amyloid fibril-forming disease.

Using different phage display techniques, it is possible to identify peptides that, for example, bind with high binding affinity to the Aβ peptide associated with Alzheimer's or to other fibril-forming peptides. These selected peptides are then used as constituents of agents according to the invention.

It is easier for a person skilled in the art to study the literature than to carry out methods, and this can be used without particular difficulty. The skilled practitioner can search the literature for active ingredients for this purpose, which are used against amyloid fibrils of a first disease, for example Alzheimer's disease. Without complexity, the skilled practitioner will ascertain a potential active ingredient A. This active agent can be used not only against the first disease, but according to the invention to treat and/or prevent a second viral disease which is enhanced by the same or other amyloid fibrils or which likewise forms amyloid fibrils, such as viral infections that are associated with SEVI.

A use according to the invention thus also lies in employing a known agent (such as D3 or a peptide according to SEQ ID NO: 1 to 11), which can be effectively used against a first disease, during the course of which a first type of amyloid fibrils is formed (Alzheimer's disease), to treat and/or prevent of a second disease, which s enhanced by amyloid fibrils of the first or a further type.

Compared to L-enantiomeric peptides, D-peptides are more resistant to proteases in vivo and invoke, if at all, only a weak immune response.

In one variant, the peptides according to SEQ ID NO: 1 to 11, and the homologs thereof, are substantially, preferably at least 60%, 75%, 80%, particularly preferably 85%, 90%, 95%, in particular 96%, 97%, 98%, 99%, or entirely, which is to say 100%, composed of D-amino acids.

The D-enantiomeric form of these peptides according to the invention is thus substantially or entirely present in the agents according to the invention.

Agents according to the invention are present as constituents, such as in tablet form or in a microbicidal gel or spray or suppositories or another form of administration, so as to treat or prevent an HIV infection.

The agents are in particular a constituent of a microbicidal gel. The object is thus also achieved by an agent, serving as a constituent of a microbicidal gel, that is suitable for preventing the formation of amyloid fibrils or for destroying the same.

For this purpose, the microbicidal gel comprises an agent containing at least one peptide, including an amino acid sequence, which was developed or invented to prevent Alzheimer's disease, in which peptides comprising this sequence prevent the formation of amyloid fibrils associated therewith or destroy the same. These may also be homologous sequences, fragments, and parts thereof. The microbicidal gel is used to treat and/or prevent HIV and/or other viral infections.

In particular, an agent which comprises a peptide including at least one amino acid sequence according to SEQ ID NO: 1 to 6, and the homologs, fragments and parts thereof, and/or polymers of SEQ ID NO: 7 to 11, and the homologs, fragments and parts thereof, is suited as a constituent of a microbicidal gel for the treatment and prevention of HIV and other viral infections.

The concentration information of the constituents, and more particularly of the peptides according to the invention, in the gel is established by a person skied in the art in an appropriate manner, as are the further constituents in the gel, such as lubricants for use in the genital area and so forth.

The same applies to the composition of a tablet used to treat HIV or treat and/or prevent HAD. The agents are in particular a constituent of a tablet. The object of the invention is thus also achieved by an agent, serving as a constituent of a tablet, which is suitable for preventing the formation of amyloid fibrils or for destroying the same.

For this purpose, the tablet comprises an agent containing at least one peptide, including an amino acid sequence, which was developed or invented to prevent Alzheimer's disease, in which peptides comprising this sequence prevent the formation of amyloid fibrils associated therewith or destroy the same. These may also be homologous sequences, fragments, and parts thereof. The tablet is used to treat and/or prevent HIV and/or other viral infections and the secondary diseases thereof, such as HAD.

In particular, an agent which comprises a peptide including at least one amino acid sequence according to SEQ ID NO.: 1 to 6, and the homologs, fragments and parts thereof, and/or polymers of SEQ ID NO: 7 to 11, and the homologs, fragments and parts thereof, is suited as a constituent of a tablet for the treatment and prevention of HIV and other viral infections, but also of secondary diseases.

The concentration information of the constituents, and more particularly of the peptides according to the invention, in the tablet, is established by a person skilled in the art in an appropriate manner, as are the other constituents of the tablet.

As described for the gel or the tablet, other described forms of administration, such as a spray or an injection solution or infusion solution, or a suppository, will also include the agents according to the invention.

Particularly advantageously, the peptide according to the invention, such as D3 according to SEQ ID NO: 1, and the polymer, such as D3D3 according to SEQ ID NO: 9, can effectively or completely prevent the enhancement of HIV infections mediated by Aβ fibrils and that mediated by SEVI fibrils at the same time.

Within the scope of the invention, it was found that findings from the prior art, in particular from Wojtowicz et al., are of purely theoretical significance, since a concurrence of Aβ fibrils, HIV particles and CD4-positive cells is anything but obvious and was considered precluded under normal conditions in the body (blood-brain barrier).

As was already mentioned, however, the prognosis of patients infected with HIV has considerably improved in recent years as a result of the therapy that is available today (HAART). The therapy must be conducted for life, since the viral infection is generally only suppressed, but not cured. It was thus found within the scope of the invention that many HIV-positive patients develop neurological deficits two to three decades after becoming infected, which are summarized, among other things, under the term "HIV-associated dementia" (HAD). It was found that, due to the high number of HIV-positive long-term survivors, HAD has become the most common form of dementia in people under the age of 50. The development of HAD has yet to be resolved. It is assumed that HIV overcoming the blood-brain barrier should be an extremely rare event. In particular, it must be assumed that HIV is able to replicate only very inefficiently, if at all, in the cells of the central nervous system (CNS). Regardless of all the existing information that is known about HIV, it is assumed today that the formation of initial Aβ fibrils starts several decades prior to the development of the first clinically observable symptoms of "Alzheimer's."

What is decisive for the present invention is the following hypothesis, which was in no way obvious heretofore. Assuming that initial Aβ fibrils have already formed and are present in the brain of a 40-year-old person, it would be conceivable that individual HIV particles that overcome the blood-brain barrier encounter Aβ fibrils there, which allow them, by virtue of the multifold increase in the infection efficiency thereof, to infect cells of the CNS and multiply in these, ultimately damaging the brain such that HAD symptoms arise. This hypothesis is supported by the results of the present patent application. While the few Aβ fibrils that are already present in the CNS at the age of approximately 40 do not cause any recognizable damage themselves, their number increases with growing age. This would explain that, despite HAART, an HIV infection can result in HAD in middle-aged individuals. The agents according to the invention effectively counteract this progression by preventing the formation of amyloid fibrils, such as the Aβ fibrils of Alzheimer's disease, or by destroying the same. The agents according to the invention directly influence the increased infectivity of virus particles, such as HIV, triggered by the fibrils. The increased infectivity caused by amyloid fibrils of Alzheimer's disease and/or fibrils associated with SEVI can be completely prevented according to the invention, and be reset to the low, natural degree of infectivity of the viruses in the absence of amyloid fibrils.

In one embodiment of the invention, agents are thus used to simultaneously treat and/or prevent fibrils associated with Alzheimer's disease and/or HIV and/or other viral diseases, and the secondary diseases thereof, such as HAD, with high binding affinity. The binding affinity exists in particular to Aβ amyloid fibrils with a dissociation constant in the range of micromolar, preferably submicromolar, particularly preferably nanomolar, most particularly preferably of a maximum of 10 picomolar and subpicomolar. This prerequisite is met by the peptide having SEQ ID NO: 9, for example, which is to say by D3D3, and other peptides according to the invention.

DESCRIPTION OF THE PREFERRED EMBODIMENTS

The invention will be described in more detail hereafter based on exemplary embodiments and the accompanying figures, without thereby limiting the scope of the present invention available to the person skilled in the art.

Exemplary Embodiment 1: Use of the Amyloidogenic Inhibitor D3 for Reducing the SEVI- or Aβ-Mediated Viral Infection So as to analyze the effect of the amyloidogenic inhibitor D3 as a potential therapeutic agent for reducing amyloid peptide-promoted retroviral propagation, adherently growing TZM-bl cells were infected with HIV-1. These cells express the HIV-1 receptors CD4, CXCR4 and CCR5, which is why they are permissive both for T-tropic and M-tropic HIV isolates. Furthermore, they express the reporter genes β-galactosidase and luciferase under the control of the HIV-1 LTR promoter, the expression of which can thus be induced by an HIV-1 infection and consequently demonstrated. The TZM-bl indicator cell line thus allows a quantitative analysis of HIV infection efficiency.

TZM-bl cells were infected with equal amounts of HIV-1, which had previously been incubated with different concentrations of $A\beta_{1-42}$ fibrils, which, in turn, had been treated with two concentrations of the peptide D3 or PBS as solvent control. D3 was composed of amino acids of the D-enantiomeric form. Forty-eight hours after infection, the TZM-bl cells were washed with PBS, fixed by adding formaldehyde/glutaraldehyde, and subsequently washed again. The β-galactosidase-induced blue coloration of the cells was carried out by incubation overnight with a X-Gal solution. The coloring solution was removed the following day, the fixed cells were washed again with PBS and analyzed for blue coloration by way of optical microscopy. Since these reporter cells also express luciferase, in addition to the β-galactosidase, proportionally with the infection rate, this effect could also be determined quantitatively. For this purpose, the cells were infected in the same manner and, after being washed twice with PBS, were lysed using 1× passive lysis buffer (PLB). After adding luciferase substrate solution, the light intensity at the 560 nm wavelength created by the oxidation of luciferin, which, in turn, is catalyzed by the firefly luciferase enzyme, was measured.

Based on the number of cells colored in blue and the measured light intensity, it was possible to demonstrate that D3 was able to considerably reduce both the infection rate promoted by SEVI and that promoted by Aβ.

Consequently, D3 according to SEQ ID NO: 1 represents a potential therapeutic agent for containing and preventing viral infections, in particular, but not exclusively, HIV and the secondary diseases thereof, such as HAD.

In addition to the role that amyloids play in the efficiency of the infection of HIV particles in sperm, it is to be assumed that amyloids also play an important role in the development of HIV-associated dementia (HAD).

20 to 30% of HIV-positive patients develop HAD, also referred to as HIV encephalopathy, during the course of the infection. It is a syndrome involving cognitive and motor dysfunction and behavioral disorders. These include motor symptoms involving impaired fine motor skills, cognitive symptoms such as impaired memory and concentration, emotional symptoms such as loss of initiative and drive, and social withdrawal with a loss of interpersonal skills.

FIG. 1 shows that $A\beta_{1-42}$ fibrils associated with Alzheimer's disease, but not monomers and oligomers, increase the HIV-1 infection of TZM-bl cells.

Equal amounts of HIV-1 isolate NL4-3 were pre-incubated for 5 min at room temperature with the indicated concentrations of $A\beta_{1-42}$ fibrils.

Thereafter, TZM-bl reporter cells were infected with pretreated virus particles.

Figure 1A:
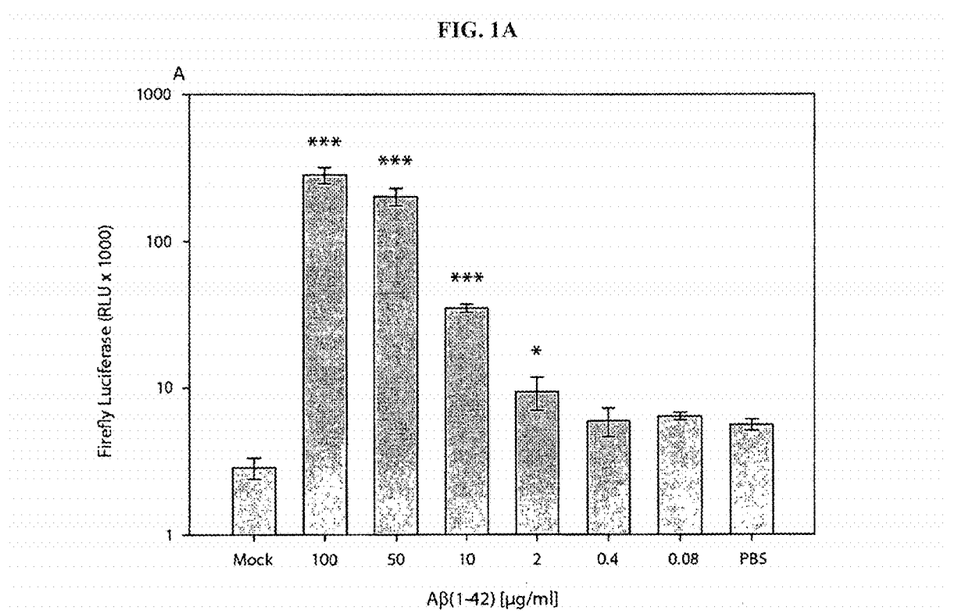
FIG. 1A shows the infection-induced luciferase activity 48 hours after infection.
Figure 1B:
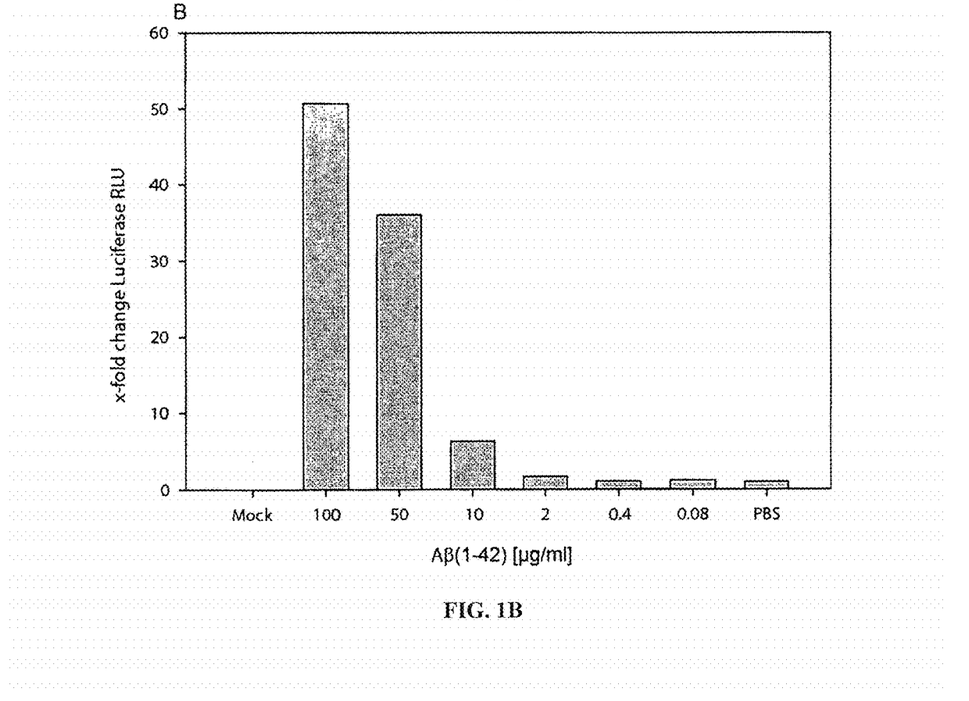
FIG. 1B shows the change in the luciferase increase relative to cells that were infected in the absence of $A\beta_{1-42}$ fibrils (mock approach).
Figure 1C:
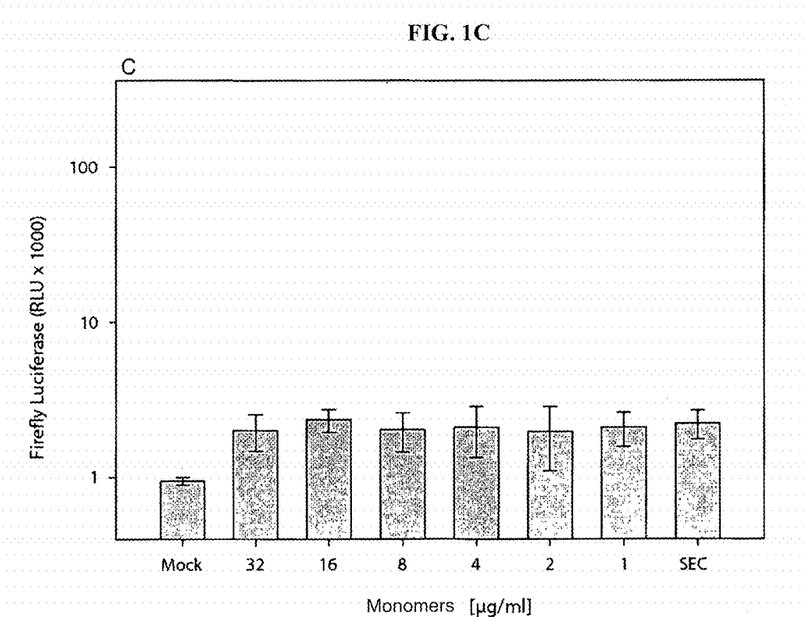
FIG. 1C show the same approach as in FIG. 1A, using the indicated amounts of $A\beta_{1-42}$ monomers and oligomers.
Figure 1D:
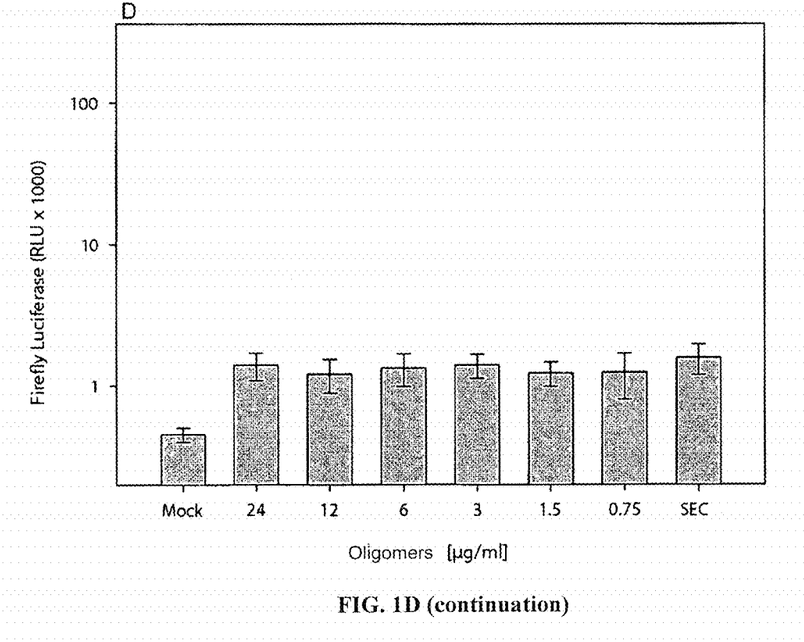
FIG. 1D show the same approach as in FIG. 1A, using the indicated amounts of $A\beta_{1-42}$ monomers and oligomers.

FIG. 1A shows the infection-induced luciferase activity 48 hours after infection. FIG. 1B shows the change in the luciferase increase relative to cells that were infected in the absence of $A\beta_{1-42}$ fibrils (mock approach). FIG. 1C and FIG. 1D show the same approach as in FIG. 1 A, using the indicated amounts of $A\beta_{1-42}$ monomers and oligomers.

Figure 1E:
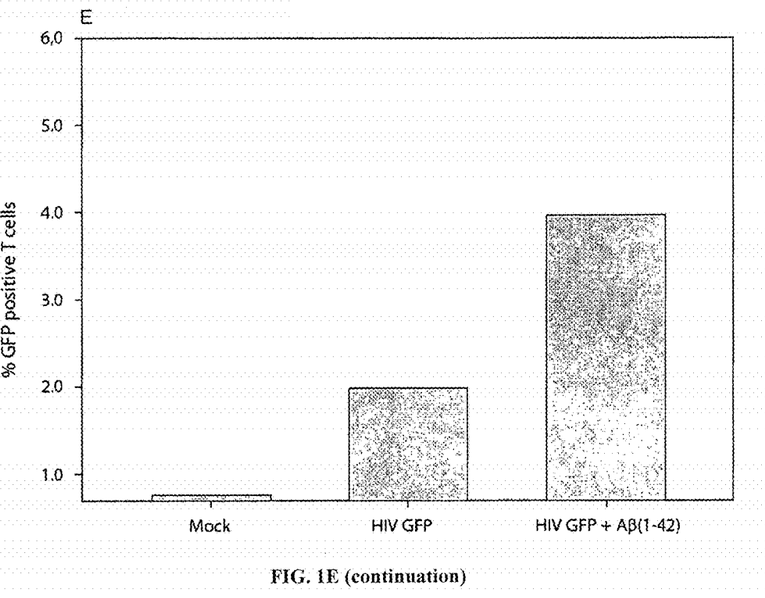
FIG. 1E shows the infectivity boosted by $A\beta_{1-42}$ fibrils in MOLT-4 T cells.

FIG. E shows the infectivity boosted by $A\beta_{1-42}$ fibrils in MOLT-4 T cells. Equal amounts of HIV-1 NL4-3 derivatives expressing an NEF-GFP fusion protein were pre-incubated for 5 min at room temperature with $A\beta_{1-42}$ [50 µg/ml]. The pretreated virus was subsequently used to infect MOLT-4 T cells. The illustration shows the percentage of GFP-positive cells, indicated by FACS analysis, 48 hours after infection.

RLU: relative light units

SEC: Size exclusion chromatography buffer (without tween)

Based on this, it is derived that peptides which effectively set the conditions for Alzheimer's disease by impairing or preventing the associated fibrils can also be used to treat and prevent HIV, and more particularly to treat and prevent HAD.

Figure 2A:
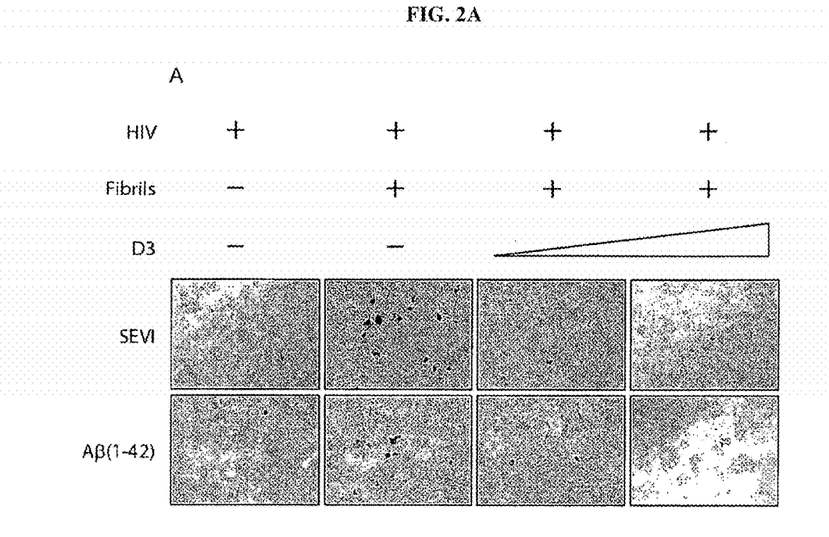
FIG. 2A shows proof of this thesis.

FIG. 2A shows proof of this thesis.

The D-peptide D3 according to SEQ ID NO: 1 acts as a potent amyloidogenic inhibitor. D3 reduces the fibril-driven infectivity, which is recognizable from the decreasing X-Gal coloration of the TZM-bl cells with increasing D3 concentration, the cells having been infected with HIV-1 in the presence (plus sign) or in the absence of SEVI and $A\beta_{1-42}$ fibrils (50 µg/ml) (minus sign). The fibrils were pre-incubated with D3 prior to infection (0.5 and 5 µg/ml).

Figure 2B:
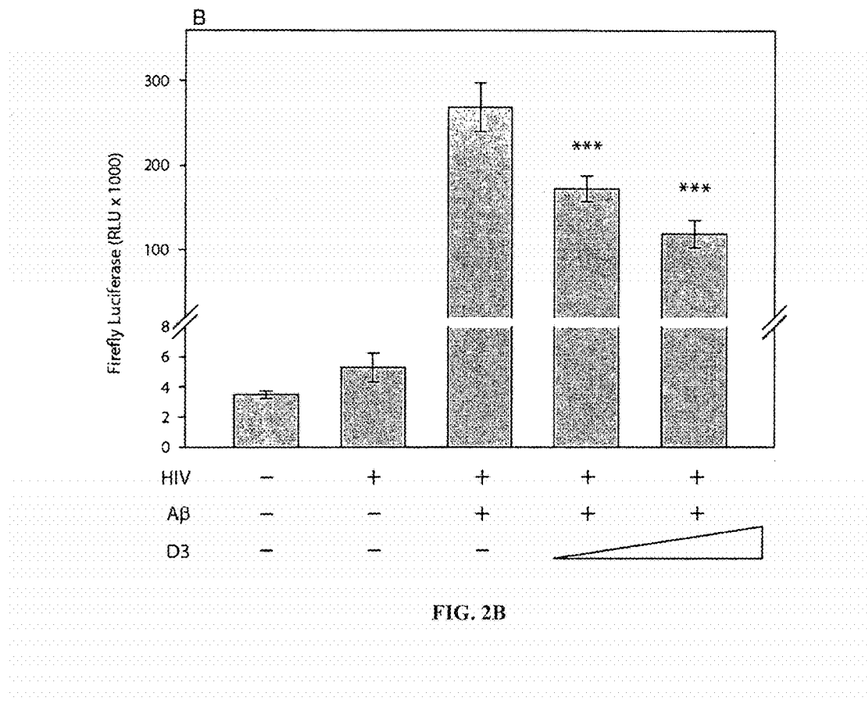
FIG. 2B shows a blot in which equal amounts of the HIV-1 strain NL4-3 were pre-incubated for 5 min at room temperature with $A\beta_{1-42}$ fibrils (50 μg/ml).

FIG. 2B shows a blot in which equal amounts of the HIV-1 strain NL4-3 were pre-incubated for 5 min at room temperature with $A\beta_{1-42}$ fibrils (50 µg/ml). In addition, fibrils were pre-incubated with D3 (0.5 and 5 µg/ml). Subsequently, the pretreated virus was used to infect TZM-bl reporter cells, and the infection-reduced luciferase activity was measured 48 hours post-infection (*** p<0.001).

Figure 2C:
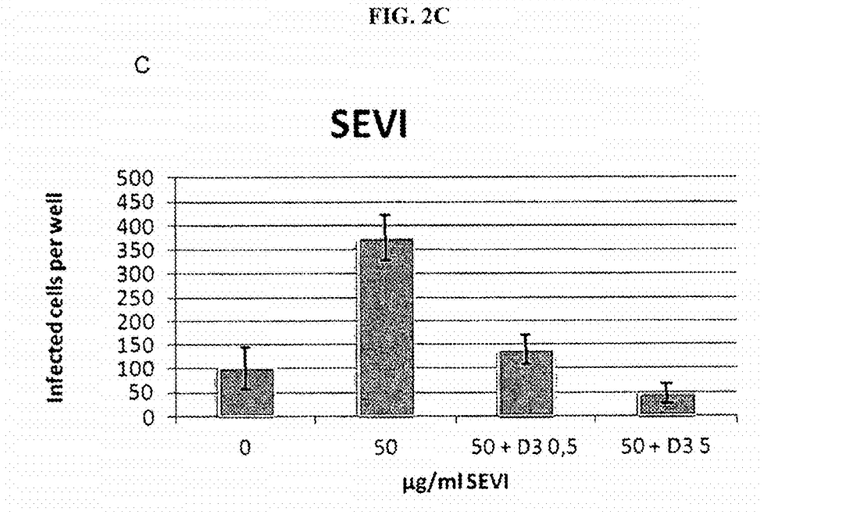
FIG. 2C shows that the number of infected cells decreases with 0.5 μg/ml D3, by approximately 60% as compared to the untreated cells with SEVI fibrils.
Figure 2D:
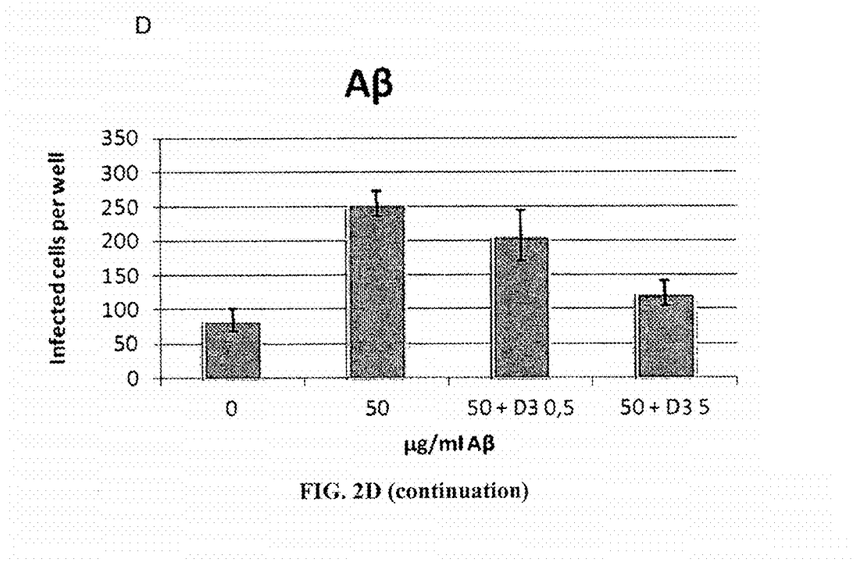
FIG. 2D shows when using 5 μg/ml D3, the number of infected cells decreases by approximately 90% compared to the untreated cells with amyloid beta fibrils.

FIG. 2C shows that the number of infected cells decreases with 0.5 µg/ml D3, by approximately 60% as compared to the untreated cells with SEVI fibrils. When using 5 µg/ml D3, the number of infected cells decreases by approximately 90% compared to the untreated cells with amyloid-beta fibrils (FIG. 2D).

Figure 3A:
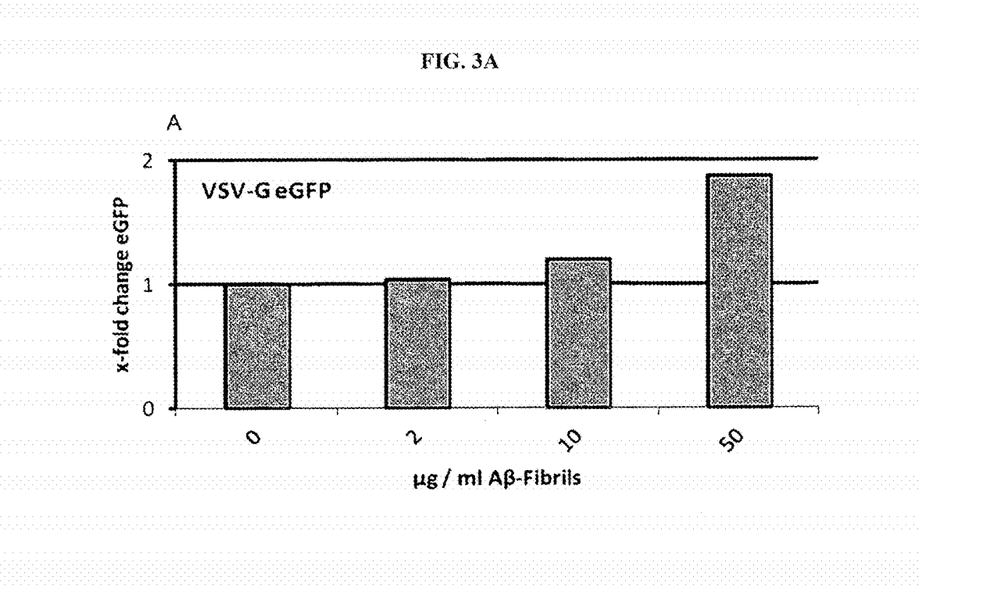
FIG. 3A shows that Aβ (1-42) fibrils are also able to promote the infection rate of pseudo typed HIV particles.
Figure 3B:
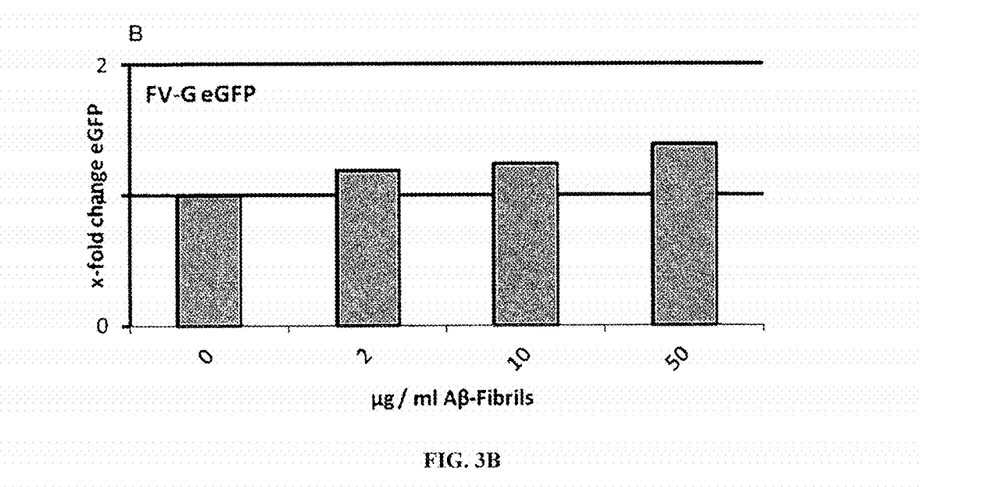
FIG. 3B shows that Aβ (1-42) fibrils are also able to promote the infection rate of pseudo typed HIV particles.

FIG. 3 shows that Aβ (1-42) fibrils are also able to promote the infection rate of pseudotype HIV particles. For this purpose, infectious virus particles were generated with the aid of lentiviral vectors, in which the viral genome was substituted with the green fluorescent gene (GFP) product. For pseudotyping, which is to say the incorporation of HIV-foreign glycoproteins, the G-protein of the vesicular stromatitis virus (VSV-G), a rhabdovirus, and the glycoprotein of the foamy virus (FV-G), a retrovirus, were used. Both glycoproteins bind to phospholipids, which are ubiquitous on the cell membrane and thereby enable a brooder host spectrum. The pseudotyped lentiviral particles were incubated for 5 min with the indicated concentration of Aβ(1-42). Subsequently, the viruses were used to transduce HEK293 T cells, which is to say to integrate the GFP gene product into the host genome in a stable manner. The number of GFP positive, which is to say transduced, cells, was analyzed 48 hours after transduction by way of FACS. The illustration shows the x-fold rise in transduced cells in relation to those that were transduced without the addition of Aβ(1-42).

This enhancing effect was less effective compared to the HIV-1 glycoprotein, but considerable. The presence of fibrils can demonstrably enhance the infection rate of viruses, regardless of the glycoproteins and regardless of the host spectrum. D3 is consequently also suited for treating other viral diseases and the secondary diseases thereof, such as in particular HAD.

Figure 4:
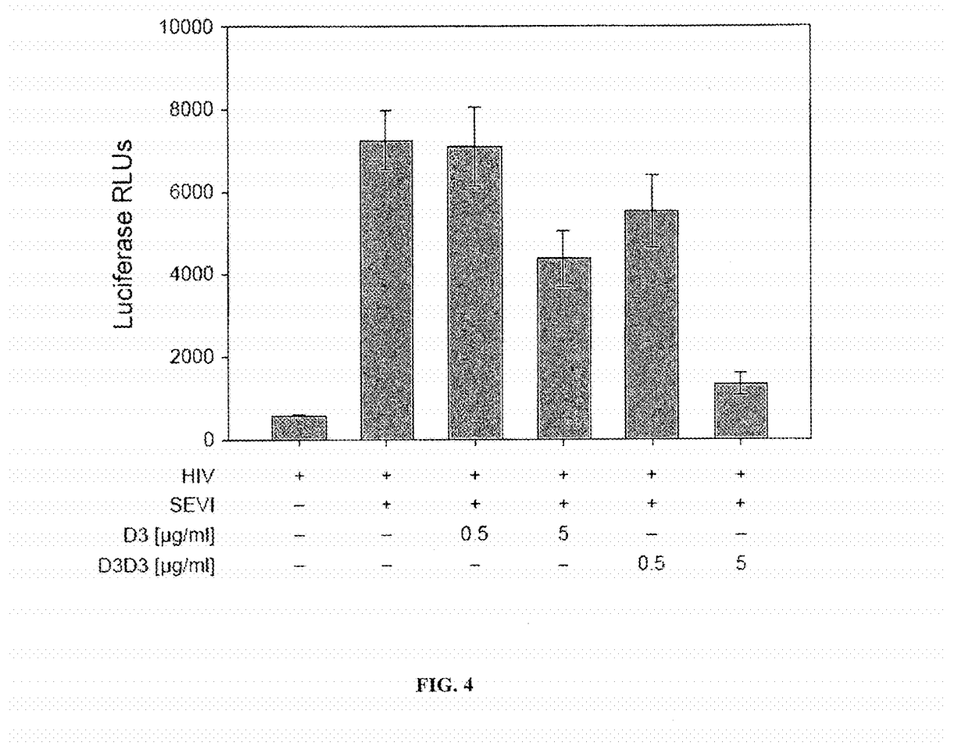
FIG. 4 and Table 1 prove, by way of example based on the inhibitors D3 and D3D3, that these also reduce the infectivity of HIV-1 increased by SEVI fibrils.

FIG. 4 and Table 1 prove, by way of example based on the inhibitors D3 and D303, that these also reduce the infectivity of HIV-1 increased by SEVI fibrils.

The test approach was broken down as follows: The reporter cell line TZM-bl was incubated with the HIV-1 laboratory strain NL4-3 PI 952 in the presence of 6 µg/ml SEVI fibrils (fibril-forming PAP fragments isolated from semen; semen derived enhancer of virus infection). The fibrils were pre-Incubated with or without D3 and D3D3 (0.5 and 5 µg/ml, respectively) prior to infection. The infection efficiency was determined by measuring the luciferase activity (introduced by a luciferase gene coded in the laboratory strain) of the infected cells 48 hours after infection (Table 1: Results of FIG. 4).

| Sample description | Mean value | Standard deviation |
| --- | --- | --- |
| HIV + PBS | 579.0 | 21.3 |
| HIV + SEVI | 7264.0 | 704.4 |
| HIV + SEVI + 0.5 D3 | 7112.7 | 959.5 |
| HIV + SEVI + 5 D3 | 4368.0 | 676.7 |
| HIV + SEVI + 0.5 D3D3 | 5529.7 | 890.8 |
| HIV + SEVI + 5 D3D3 | 1321.0 | 252.7 |

The results show that the peptides D3, and more particularly D303, lower the increased infectivity of the viruses caused by fibrils associated with SEVI by approximately 80%.

The invention claimed is:

1. An agent, comprising at least one substance that is suitable for inhibiting formation of amyloid fibrils, which increase infection efficiency of human immunodeficiency virus (HIV), or for destroying the HIV, for application in a method to treat and/or prevent HIV infection and/or acquired immunodeficiency syndrome (AIDS) and/or a secondary disease of HIV infection, by using the substance to prevent formation of the amyloid fibrils, wherein the substance comprises at least one peptide which (i) includes an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, homologs of said peptides with an identity of at least 80%, and combinations thereof, and (ii) is substantially or entirely composed of D-amino acids.

2. The agent according to claim 1, wherein the agent has a binding affinity to the amyloid fibrils with a dissociation constant in the range of micromolar, submicromolar, or nanomolar.

3. A method for therapeutically treating and/or for preventing a viral infection and/or a secondary disease thereof in a human, comprising administering the agent according to claim 1.

4. The method according to claim 3, wherein the viral infection and/or a secondary disease is at least one of HIV and HAD.

5. The method according to claim 3, comprising simultaneous therapeutic treatment and/or prevention of Alzheimer's disease and of HIV and/or HAD as the secondary disease and/or other secondary diseases.

6. A microbicidal gel, comprising at least one agent according to claim 1.

7. The microbicidal gel according to claim 6, wherein the agent is adapted for prevention of HIV and/or other viral infections and of HAD as a secondary disease and/or other secondary diseases.

8. The microbicidal gel according to claim 6, wherein the microbicidal gel is adapted for use in a genital area.

9. A tablet, comprising at least one agent according to claim 1.

10. The tablet according to claim 9, wherein the agent is adapted for treatment of HIV and/or other viral infections and HAD as a secondary disease and/or other secondary diseases.

11. An injection solution or infusion solution, comprising at least one agent according to claim 1.

12. The agent according to claim 1, wherein the peptide is RD2 peptide comprising SEQ ID NO: 2.

13. The agent according to claim 1, wherein the amino acid sequence is a homolog of SEQ ID NO: 5, SEQ ID NO: 6, SEQ ID NO: 7, SEQ ID NO: 8, or SEQ ID NO: 10, with an identity of at least 80%.

* * * * *

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: D3

<400> SEQUENCE: 1

Arg Pro Arg Thr Arg Leu His Thr His Arg Asn Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: RD2

<400> SEQUENCE: 2

Pro Thr Leu His Thr His Asn Arg Arg Arg Arg Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: DB3

<400> SEQUENCE: 3

Arg Pro Ile Thr Arg Leu Arg Thr His Gln Asn Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: D3r

<400> SEQUENCE: 4

Arg Pro Arg Thr Arg Leu His Thr His Arg Asn Arg Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: D3p

<400> SEQUENCE: 5
```

Arg Pro Arg Thr Arg Leu His Thr His Arg Asn Arg Pro
1               5                   10

<210> SEQ ID NO 6
<211> LENGTH: 13
<212> TYPE: PRT
<213> ORGANISM: Artificial Sequence
<220> FEATURE:
<223> OTHER INFORMATION: D3a

<400> SEQUENCE: 6

Arg Pro Arg Thr Arg Leu His Thr His Arg Asn Arg Ala
1               5                   10

<210> SEQ ID NO 7
<211> LENGTH: 24
<212> TYPE: PRT
<213> ORGANISM: Artificial Sequence
<220> FEATURE:
<223> OTHER INFORMATION: RD2D3

<400> SEQUENCE: 7

Pro Thr Leu His Thr His Asn Arg Arg Arg Arg Arg Arg Pro Arg Thr
1               5                   10                  15

Arg Leu His Thr His Arg Asn Arg
            20

<210> SEQ ID NO 8
<211> LENGTH: 24
<212> TYPE: PRT
<213> ORGANISM: Artificial Sequence
<220> FEATURE:
<223> OTHER INFORMATION: D3RD2

<400> SEQUENCE: 8

Arg Pro Arg Thr Arg Leu His Thr His Arg Asn Arg Pro Thr Leu His
1               5                   10                  15

Thr His Asn Arg Arg Arg Arg Arg
            20

<210> SEQ ID NO 9
<211> LENGTH: 24
<212> TYPE: PRT
<213> ORGANISM: Artificial Sequence
<220> FEATURE:
<223> OTHER INFORMATION: D3D3

<400> SEQUENCE: 9

Arg Pro Arg Thr Arg Leu His Thr His Arg Asn Arg Pro Arg Thr
1               5                   10                  15

Arg Leu His Thr His Arg Asn Arg
            20

<210> SEQ ID NO 10
<211> LENGTH: 24
<212> TYPE: PRT
<213> ORGANISM: Artificial Sequence
<220> FEATURE:
<223> OTHER INFORMATION: RD2RD2

<400> SEQUENCE: 10

Pro Thr Leu His Thr His Asn Arg Arg Arg Arg Arg Pro Thr Leu His
1               5                   10                  15

Thr His Asn Arg Arg Arg Arg Arg

```
<210> SEQ ID NO 11
<211> LENGTH: 24
<212> TYPE: PRT
<213> ORGANISM: Artificial Sequence
<220> FEATURE:
<223> OTHER INFORMATION: DB3DB3

<400> SEQUENCE: 11

Arg Pro Ile Thr Arg Leu Arg Thr His Gln Asn Arg Arg Pro Ile Thr
1               5                   10                  15

Arg Leu Arg Thr His Gln Asn Arg
            20
```